US009551768B2

(12) United States Patent
Cistola et al.

(10) Patent No.: US 9,551,768 B2
(45) Date of Patent: Jan. 24, 2017

(54) NMR METHOD FOR MONITORING CHANGES IN THE CORE OF LIPOPROTEIN PARTICLES IN METABOLISM AND DISEASE

(71) Applicant: East Carolina University, Greenville, NC (US)

(72) Inventors: David P. Cistola, Fort Worth, TX (US); Michelle Robinson, Greenville, NC (US)

(73) Assignee: East Carolina University, Greenville, NC (US)

( * ) Notice: Subject to any disclaimer, the term of this patent is extended or adjusted under 35 U.S.C. 154(b) by 720 days.

(21) Appl. No.: 13/839,420

(22) Filed: Mar. 15, 2013

(65) Prior Publication Data

US 2014/0273247 A1    Sep. 18, 2014

(51) Int. Cl.
*G01N 24/00* (2006.01)
*G01N 33/92* (2006.01)
(Continued)

(52) U.S. Cl.
CPC ......... *G01R 33/448* (2013.01); *A61B 5/14546* (2013.01); *A61B 5/7275* (2013.01); *G01N 24/08* (2013.01); *A61B 5/055* (2013.01)

(58) Field of Classification Search
CPC . G01R 33/465; G01R 33/5601; G01R 33/302; G01R 33/448; G01R 33/44; G01R 33/50; A61K 49/14; A61K 49/227; A61K 51/0404; A61K 51/1224
See application file for complete search history.

(56) References Cited

U.S. PATENT DOCUMENTS

| 4,933,844 A | 6/1990 | Otvos |
| 5,192,264 A | 3/1993 | Fossel |

(Continued)

FOREIGN PATENT DOCUMENTS

| CA | 1327993 C | 3/1994 |
| EP | 0 361 214 B1 | 7/1994 |

(Continued)

OTHER PUBLICATIONS

Aursand et al. "Low Field NMR Studies of Atlantic Salmon (*Salmo salar*)", Modern Magnetic Resonance, ed. Webb, 2008, pp. 905-913.*

(Continued)

*Primary Examiner* — Yelena G Gakh
(74) *Attorney, Agent, or Firm* — Parsons Summa

(57) ABSTRACT

A method is disclosed for measuring the properties of protein and lipoprotein elements in a sample. The method includes the of placing a small volume of a sample into a NMR instrument tuned to measure a particular nucleus, applying a series of radiofrequency pulses with intermittent delays in order to measure spin-spin and/or spin-lattice relaxation time constants from the time-domain decay of the signal, without the use of chemical shifts and without converting data into the frequency domain by Fourier transform or other means, at least partially suppressing the water signal prior to the beginning of a sequence used to record relaxation time constants in the time domain, optionally utilizing relaxation contrast agents or other chemical additives to perturb the solvent water or other elements of the sample, analyzing the exponentially decaying NMR signal in the time domain using multi-exponential analysis, and comparing differences in the relaxation time constants for lipoprotein- or protein-specific elements within a single human subject, or between subjects, to assess normal and (Continued)

abnormal metabolism reflective of increased disease risk or active disease.

3 Claims, 6 Drawing Sheets

(51) Int. Cl.
*G01R 33/44* (2006.01)
*G01N 24/08* (2006.01)
*A61B 5/145* (2006.01)
*A61B 5/00* (2006.01)
*A61B 5/055* (2006.01)

(56) References Cited

U.S. PATENT DOCUMENTS

| | | | |
|---|---|---|---|
| 5,343,389 | A | 8/1994 | Otvos |
| 5,366,440 | A | 11/1994 | Fossel |
| 6,426,058 | B1 | 7/2002 | Pines et al. |
| 6,518,069 | B1 | 2/2003 | Otvos et al. |
| 6,574,495 | B1 | 6/2003 | Golman et al. |
| 6,576,471 | B2 | 6/2003 | Otvos |
| 6,617,167 | B2 | 9/2003 | Otvos et al. |
| 6,653,140 | B2 | 11/2003 | Otvos |
| 6,683,455 | B2 | 1/2004 | Ebbels et al. |
| 6,818,202 | B2 | 11/2004 | Pines et al. |
| 7,191,069 | B2 | 3/2007 | Wishart et al. |
| 7,243,030 | B2 | 7/2007 | Reeve et al. |
| 7,306,562 | B1 | 12/2007 | Baykal |
| 7,397,241 | B2 | 7/2008 | Gauthausen et al. |
| 7,474,095 | B2 | 1/2009 | Levitt et al. |
| 7,550,971 | B2 | 6/2009 | Carpenter |
| 7,564,243 | B2 | 7/2009 | Desvaux et al. |
| 7,647,234 | B1 | 1/2010 | Ruderman et al. |
| 7,713,744 | B2 | 5/2010 | Benner et al. |
| 7,750,633 | B2 | 7/2010 | Pines et al. |
| 7,790,465 | B2 | 9/2010 | Otvos |
| 2002/0087276 | A1 | 7/2002 | Otvos |
| 2003/0054599 | A1 | 3/2003 | Huizing et al. |
| 2003/0119194 | A1 | 6/2003 | Otvos |
| 2004/0098208 | A1 | 5/2004 | Reeve et al. |
| 2004/0142496 | A1 | 7/2004 | Nicholson et al. |
| 2005/0222504 | A1 | 10/2005 | Otvos et al. |
| 2006/0104906 | A1 | 5/2006 | Ardenkjaer-Larsen et al. |
| 2006/0183234 | A1 | 8/2006 | Otvos |
| 2007/0063700 | A1 | 3/2007 | Levitt et al. |
| 2007/0178598 | A1 | 8/2007 | Jeyarajah et al. |
| 2007/0264677 | A1 | 11/2007 | Otvos |
| 2008/0038829 | A1 | 2/2008 | Kremer et al. |
| 2008/0088308 | A1 | 4/2008 | Carpenter et al. |
| 2008/0204014 | A1 | 8/2008 | Desvaux et al. |
| 2009/0219022 | A1 | 9/2009 | Carpenter et al. |
| 2010/0039109 | A1 | 2/2010 | Cheng et al. |
| 2010/0100334 | A1 | 4/2010 | Otvos |
| 2010/0219826 | A1 | 9/2010 | Duckett et al. |
| 2010/0233089 | A1 | 9/2010 | Ross et al. |

FOREIGN PATENT DOCUMENTS

| | | |
|---|---|---|
| WO | 9104744 A1 | 4/1991 |
| WO | 9110128 A1 | 7/1991 |
| WO | 0017766 A2 | 11/2000 |
| WO | 0065366 A1 | 11/2000 |
| WO | 03012416 A1 | 2/2003 |
| WO | 2006/076631 A1 | 7/2006 |
| WO | 2009/129265 A1 | 10/2009 |

OTHER PUBLICATIONS

Mo and Raftery, "Pre-SAT180, a Simple and Effective Method for Residual Water Suppression", J. Magn. Reson., 2008, v. 190, No. 1, pp. 1-6.*

Bubici et al. "Inversion of Multi-component FFC-NMR relaxation decays", STELAR, Sep. 2012, pp. 1-3.*

MickLander et al. "Multivariate Analysis of Time Domain NMR Signals in Relation to Food Quality", in Magnetic Resonance in Food Science, 2003, ed. Belton et al., pp. 239-254.*

Bell et al., "Effects of n-3 fatty acids on the NMR profile of plasma lipoproteins", J. Lipid Research, 1996, v. 37, pp. 1664-1674.*

Tang et al. "Use of relaxation-edited one-dimensional and two dimensional nuclear magnetic resonance spectroscopy to improve detection of small metabolites in blood plasma", Anal. Biochem., 2004, v. 325, pp. 260-272.*

Mallol et al. "Human serum/plasma lipoprotein analysis by NMR: Application to the study of diabetic dyslipidemia". Prog. Nucl. Magn. Reson., 2013, (published on-line Sep. 11, 2012), v. 70, pp. 1-24.*

Miller et al., Seven Direct Methods for Measuring HDL and LDL Cholesterol Compared with Ultracentrifugation Reference Measurement Procedures, Clinical Chemistry 56:6, 2010, pp. 977-986.

Choi et al., N.m.r. Lipid Profiles of Cells, Tissues and Body Fluids—Neutral non-acidic and acidic phospholipid analysis of Bond Elut chromatographic fractions; Biochem Journal, 1993, pp. 712-721.

Hayes et al., Effect of a high saturated fat and no-starch diet on serum lipid subfractions in patients with documented atherosclerotic cardiovascular disease; Mayo Clinic Procedures, vol. 78, Issue 11; Nov. 1, 2003; pp. 1-6.

Spin-lattice relaxation time; from Wikipedia; accessed Jan. 21, 2011 at http://en.wikipedia.org/wiki/Spin-lattice_relaxation_time; pp. 2.

Bruker Optics; Principles of NMR; accessed Jan. 21, 2011 at http://www.brukeroptics.com/nmr_principles.htmll?&L=0 &print=1.

Total Cholesterol Certification Protocol for Manufacturers—Revised; CRMLN Revised Total Cholesterol Certification Protocol; Oct. 2004; pp. 1-17.

Cistola; Benchtop Time-doman NMR Methods and Tools for Assessing Serum Lipoprotein Particle Properties and Cardiovascular Disease Risk; Sep. 30, 2010; 16 pages.

Robinson et al, Lipoprotein Remodeling in Human Serum as Monitored by Benchtop Time-Doman NMR; 2012.

Eaton et al., Spin Lattice Relaxation in Solution and Summary of Relaxation Mechanisms; University of Denver Department of Chemistry and Biochemistry; Presented at Modern EPR Spectroscopy Euro-Summer School in Retie, Belgium, Dec. 1-7, 2002.

Barkemeyer et al., Heteronuclear Polarization Transfer Using Selective Pulses during Hydrogenation with Parahydrogen; Journal of Magnetic Resonance, Series A 120, (1996) pp. 129-132.

* cited by examiner

NMR METHOD FOR MONITORING CHANGES IN THE CORE OF LIPOPROTEIN PARTICLES IN METABOLISM AND DISEASE

BACKGROUND

The present invention relates to the analysis of blood to identify and measure properties that correlate with cardiovascular disease.

Cardiovascular disease—primarily in the form of heart attack or stroke—is the leading cause of death in the United States and other developed countries. Cardiovascular disease is likewise becoming an increasing cause of death in developing countries as the risk of death from infectious diseases decreases in such countries.

Some of the main risk factors associated with cardiovascular disease are generally well understood. They include an elevated amount of low density lipoprotein (LDL), high blood pressure, cigarette smoking, diabetes mellitus ("diabetes"), family history, and a less physically active, more sedentary lifestyle.

Serum LDL cholesterol levels are positively correlated with cardiovascular disease risk. However, approximately half of patients who suffer from symptomatic coronary artery disease have normal LDL-cholesterol concentrations. Therefore, there appears to be a hidden risk not detected by conventional clinical laboratory measurements of cholesterol.

As currently best understood, cholesterol deposited in arteries represents a main factor in cardiovascular disease. Cholesterol is effectively insoluble in water and blood and thus the body carries cholesterol using particles called lipoproteins. The body uses several lipid transporting particles present in blood and these lipoprotein particles are typically referred to as chylomicrons, very low density lipoproteins (VLDL), intermediate density lipoproteins (IDL) and high density lipoproteins (HDL). Density increases when less cholesterol is present and density decreases when more cholesterol is present. Thus, the layman often refers to LDL cholesterol as "bad" cholesterol and HDL cholesterol as "good" cholesterol.

Low density lipoprotein particles tends to deposit in artery walls to form atherosclerotic plaques in the artery. In turn, the deposition of LDL to form the atherosclerotic plaques is promoted by an increased LDL concentration (or remnants that can form LDL particles) and a decreased LDL particle size.

In order to help predict and potentially moderate or avoid cardiovascular disease in individuals, conventional clinical tests are carried out to measure certain of the known risk factors. Currently, the most common test is the basic lipid panel which measures total cholesterol, HDL cholesterol ("HDL-C"), and triglycerides. The LDL cholesterol ("LDL-C") is calculated as the difference between total cholesterol and HDL cholesterol.

Currently, approximately 250,000,000 such tests are carried out in the United States every year, and on a worldwide basis 540 million tests are carried out each year. Current costs are between about $26 and $56 per test.

As an additional factor, LDL can be present in different LDL particle sizes. In turn, smaller LDL particle sizes are associated with an increased risk of cardiovascular disease. Because of the size relationship, information about the size of the LDL particles is valuable in combination with information about the concentration of LDL particles.

Currently, the common tests for measuring LDL particle size include vertical autoprofile (VAP®), gradient gel electrophoresis, and NMR lipoprofiles.

VAP is also referred to as a vertical spin density gradient ultracentrifugation and an exemplary version ("The VAP Cholesterol Test"®) is provided by Atherotech, Inc. of Birmingham, Ala. (USA).

Gradient gel electrophoresis distinguishes particle size in a otherwise conventional electrophoresis (i.e. chromatography) process with an exemplary test offered by Berkeley HeartLab Inc. of (South San Francisco Calif. (USA).

In one commercial embodiment, NMR lipoprofile testing is based upon the chemical shift of the resonant frequencies. LipoScience Inc. (Raleigh, N.C. USA) is an exemplary provider of such tests, a number of which are based on U.S. Pat. No. 5,343,389 (and others) to James D. Otvos ("the Otvos patents"). The Otvos patents employ frequency-domain FT-NMR to study lipoprotein particle properties, such as particle size and particle number, in order to perform clinical diagnostic testing and disease risk assessment. In order to provide accurate data, however, chemical shift NMR is typically carried out in large (e.g., 400 megahertz or higher) high resolution Fourier-transform NMR instruments. Many such instruments incorporate a superconducting magnet cooled by a surrounding environment of liquid helium which in turn is surrounded by liquid nitrogen. As a result, the device is large and expensive and the testing is carried out in a small number of central laboratories at a cost of between about 100 and $200 per test.

Such tests also require a frequency-domain analysis, typically performed by a Fourier transform of the data. The key measurable is the chemical shift, a measure of relative frequency and atomic environment. Differences in chemical shifts are used to distinguish and resolve different lipoprotein classes and permit the detection of particle size and number.

In evaluating an individual's lipid profile, core mobility or fluidity of the lipids is a reflection of the relative ratio of different cholesteryl ester and triglyceride molecules in the particle core, which in turn, is a reflection of normal or abnormal lipid metabolism.

Lipoproteins are the body's nanoparticle delivery systems that carry water-insoluble cholesterol and triglyceride molecules through the blood and target them to particular tissues for metabolism. Lipoprotein particles can be distinguished by their density, size, chemical composition and charge. They can also be distinguished by the relative lipid content of the particle's oily core compartment. For example, the cores of LDL and HDL are relatively rich in cholesteryl ester (a highly water-insoluble form of cholesterol), whereas VLDL and chylomicrons are relatively rich in triglycerides. Triglyceride molecules are more flexible than cholesteryl esters, so oil phases rich in triglycerides will appear more fluid and mobile, less viscous. Also, the ratio of these components and thus, the core mobility, changes with metabolism and disease.

On a broad basis, the use of NMR techniques for medical purposes is not new, and the term "NMR" typically can refer to a variety of diagnostic methods. There are many types of NMR methods and instruments and thousands of distinct NMR experiments. A vivid example of this is magnetic resonance imaging ("MRI"), which was originally called NMR Imaging. MRI is a variation of NMR that yields anatomical images rather than chemical signatures. Although MRI is based on the same fundamental physics, it involves different instrumentation, methods and derived measurable from other NMR techniques. Thus, different kinds of NMR are used in somewhat related but distinct areas of medical diagnosis, imaging, and treatment.

U.S. Pat. No. 7,550,971 B2) to Carpenter and Benson describe a method of determining analyte concentrations in body fluids such as blood plasma or serum, examples given in the claims are the concentrations of glucose, cholesterol, triglycerides, albumin, blood urea nitrogen, alkaline phosphatase and creatinine. The method is restricted to the use of low-field, bench-top TD-NMR instruments, but the measurements and derived quantities are analyte concentration rather than lipoprotein core mobility. These contrasting measurables provide completely different types of diagnostic information.

Arguably, the Carpenter and Benson methods are thinly justified and lack any preliminary data that demonstrates the feasibility of their method for measuring analyte concentrations, and bench-top TD-NMR may not be as suitable for measuring the analyte concentrations as Carpenter and Benson imply. Serum is a complex mixture, and U.S. Pat. No. 7,550,971 lacks any explanation as to how the different analytes in serum can be resolved from one another. Instead, much of the content in U.S. Pat. No. 7,550,971 reflects the known operation of the TD-NMR instrument rather than a technique for resolving analytes from TD-NMR data.

As a result of these various factors, vertical autoprofile, gradient gel electrophoresis, and NMR lipoprofiles can be impractical for routine clinical use; i.e., they are too expensive and too cumbersome to be carried out on-site in a practitioner's office or a hospital laboratory.

As another factor, various lipid tests (e.g., for HDL-C and LDL-C) can be inaccurate in certain circumstances. For example, calculated LDL-C values from a conventional lipid panel are not accurate when determined from non-fasting blood samples or in patients who have elevated triglyceride levels, as is common in diabetes. Likewise, some advanced lipid tests like the NMR LipoProfile require fasting blood samples and thus, cannot monitor changes in lipoprotein particles during metabolism following a meal.

Furthermore, evidence is beginning to emerge that characteristics of lipid-carrying particles other than size and density will correlate with an increased risk of cardiovascular disease.

As yet another factor, when any particular test is difficult to carry out, or must be carried out off-site, or will take significant time to complete, or any combination of these factors, the use of that test will tend to be less frequent than the use of tests that can be carried out quickly and easily at a location—a physician's office, small clinic, or hospital—where patients are typically located and their blood samples taken.

Thus, tests that identify cardiovascular risk and that can be carried out more quickly, more easily, less expensively, and on site would tend to be used more frequently and thus provide greater benefits to individual patients and to the relevant patient population.

Therefore, a need exists for faster, similar and localized techniques that will identify and measure relevant characteristics that correlate to an expected degree of risk of cardiovascular disease.

SUMMARY

This invention describes non-perturbing methods for monitoring changes in the core mobility and core composition of lipoprotein particles in intact, unfractionated body fluids such as blood serum or plasma.

In one aspect, the method includes the of placing a small volume of a sample into a NMR instrument tuned to measure a particular nucleus, applying a series of radiofrequency pulses with intermittent delays in order to measure spin-spin ("$T_2$") and/or spin-lattice ("$T_1$") relaxation time constants from the time-domain decay of the signal, without the use of chemical shifts and without converting data into the frequency domain by Fourier transform or other means, at least partially suppressing the water signal prior to the beginning of a sequence used to record relaxation time constants in the time domain, optionally utilizing relaxation contrast agents or other chemical additives to perturb the solvent water or other elements of the sample, analyzing the exponentially decaying NMR signal in the time domain using multi-exponential analysis, and comparing differences in the relaxation time constants for lipoprotein- or protein-specific elements within a single human subject, or between subjects, to assess normal and abnormal metabolism reflective of increased disease risk or active disease.

In another aspect, the method comprises measuring the pulsed time domain NMR spin-spin relaxation time for a plurality of LDL samples, normalizing the viscosity of the same LDL samples, plotting the product of spin-spin relaxation time and viscosity for the samples against an axis defined by spin-spin relaxation time to thereby develop a database of $T_2$ or $T_2V$ statistics (or $T_1$ or $T_1V$ statistics or some combination of $T_2$, $T_2V$, $T_1$, or $T_1V$) for the original LDL samples, measuring the classic lipoprotein profile for the same LDL samples, and correlating known risks of cardiovascular disease based upon the classic lipoprotein testing with the results as determined by the $T_2$ or $T_2V$ statistics to thereby correlate the $T_2$ or $T_2V$ statistics with the known risks of cardiovascular disease in a statistically acceptable manner. As used herein, the term "normalizing" the viscosity of the sample comprises either using samples at the same viscosity by physically manipulating the samples to obtain the viscosity; or mathematically modeling the resulting data so that the results are comparable across viscosities. Persons skilled in the art are familiar with both techniques and they are not otherwise described in detail herein.

Without being bound by theory, the possibility exists that the relevant interpretation of the NMR data can be obtained regardless of normalization; i.e., the viscosity normalization may be option or unnecessary. Thus, where appropriate the phrase "$T_2$ or $T_2V$" reflects this.

In another aspect, the invention is a diagnostic kit that includes a pulse time domain NMR instrument, a sample selected from the group consisting of serum and plasma, and a database of $T_2$ or $T_2V$ data that correlates with known cardiovascular risk statistics.

In another aspect, the invention is a combinatorial library that includes a plurality of patient samples selected from the group consisting of whole or partially fractionated serum or plasma, and a $T_2$ or $T_2V$ measurement for each sample.

In another aspect, the invention is a method of determining cardiac risk factors based upon blood samples. The method includes the steps of measuring the pulse time domain NMR spin-spin or spin-lattice relaxation time of a sample selected from the group consisting of serum and plasma, measuring the lipid profile of the same sample, optionally combining the spin-spin relaxation time and viscosity of the sample to produce a $T_2$ or $T_2V$ value for the blood sample, and comparing the $T_2$ or $T_2V$ value to the lipid profile of the sample to identify the cardiac risk measured by the $T_2$ or $T_2V$ value based upon the cardiac risk measured by the lipid profile.

DETAILED DESCRIPTION

Figure 1:
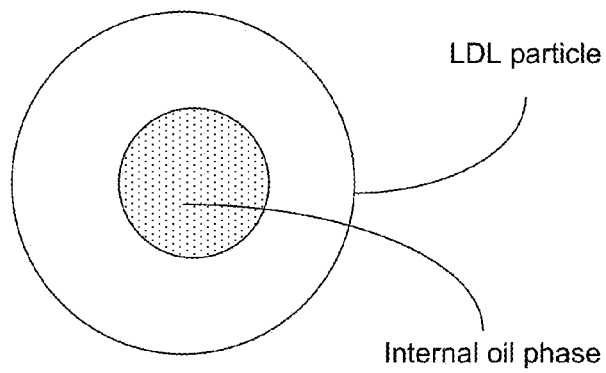
FIG. 1 is a very general schematic diagram of an LDL particle and its internal oil phase.

The methods of the invention resolve individual lipoprotein particle classes (e.g., low-density lipoprotein or LDL) by detecting differences in core lipid mobility, which is influenced by the relative amount of cholesteryl ester to triglyceride molecules within each particle's core. Variability in core mobility and core composition within a particle class, such as LDL, can result from patient-to-patient differences, or from particle remodeling within an individual subject as occurs during metabolism following a meal. Changes in lipoprotein particle core mobility and core composition are monitored using a time-domain nuclear magnetic resonance (TD-NMR) analysis. A hallmark of this approach is that the analysis is performed without Fourier transformation and without the use of frequency-domain information such as chemical shifts. Unlike frequency-domain Fourier-transform NMR, this time-domain NMR analysis can be performed at low magnetic fields (≤60 MHz for hydrogen) in a low-cost, bench-top instrument configuration, although it can also be performed in conventional high-field NMR spectrometers.

The general principles of time domain pulse NMR are generally well understood and familiar to persons of ordinary skill in the art and need not be discussed in detail. In brief, however, a sample is positioned in an external magnetic field provided by a permanent magnet. This aligns the magnetic moments of the hydrogen atoms with (or against) the permanent magnetic field. Then, a radio frequency pulse is applied in a direction that provides a secondary (temporary) magnetic field perpendicular to the permanent magnetic field. This moves the magnetic moments of the hydrogen atoms away from their equilibrium state. The time duration of the pulse determines how far the magnetic moments move. The combined movement of many spins (many hydrogen atoms) generates a small but detectable oscillating magnetic field that in turn induces an alternating voltage that is measured as the NMR signal by a detection coil.

At the end of the pulse, the protons in the sample give up excess energy to their surroundings and relax back to the equilibrium state with respect to the permanent magnetic field. This relaxation takes a certain amount of time, so that the NMR signal remains detectable for a period of time that can range from several milliseconds to several seconds.

Furthermore, the relaxing component of the NMR signal will be characteristic of individual mobility domains, which in turn, help identify the molecules involved in the motions. For example, cholesterol molecules are more internally rigid than triglyceride molecules and will tend to give lower $T_2$ and $T_1$ values.

Additionally, the data resolution of the pulse time domain NMR technique of the invention is on the order of particle size. In comparison, Fourier transfer NMR resolves data on an atomic scale. As a result, the time domain technique makes fewer technical demands (so to speak) on the instrument and can provide useful data at the available resolution.

According to the invention, it is been determined that time decay constants are sensitive to both particle size and particle mobility.

The method is also tolerant of multiple phases or mixed phases; i.e., solids and liquids in many circumstances.

As part of the correlation discoveries of the invention, it is now been determined that LDL particles with a higher triglyceride/cholesterol molecular ratio in the core have a longer spin-spin relaxation time ($T_2$) and particles with a lower triglyceride/cholesterol ratio have a shorter $T_2$.

Although the inventors do not wish to be bound by a particular theory, it appears that this may result from the characteristics of an LDL particle as not being solid in the same sense as a solid homogeneous composition would be. Instead, the LDL particle has an internal oil phase (FIG. 1). In turn, the oil phase moves (tumbles) differently—and typically faster—than the remainder of the particle. This faster internal tumbling increases the spin-spin relaxation time.

In one embodiment, the hydrogen spin-spin relaxation rate constants (or time constants) are measured using a low-field bench-top time-domain NMR analyzer, and the relaxation rate constants for individual lipoprotein classes are resolved through a multi-exponential deconvolution algorithm. Another key feature of this analysis is that measurements can be made directly on intact body fluids (e.g., serum, plasma or blood) without the need for separation or fractionation of individual lipoprotein classes by ultracentrifugation, electrophoresis, chromatography or other time-consuming, sample-perturbing methods. Because of the relative simplicity and low cost, this method has potential application to clinical testing for the detection of unique dyslipidemias and for the early detection and risk assessment of cardiovascular disease, diabetes and cancer.

The measurements can, of course, be made in conventional high-field NMR spectrometers, but as set forth herein, the use of Benchtop instruments offers a number of clinical advantages.

In the invention, time-domain NMR resolves individual lipoprotein classes by measuring mobility differences in the oil phases within the core compartment of lipoprotein particles. The invention is also based on the discovery that TD-NMR is sensitive to changes in the particle core within a lipoprotein class. For example, the LDL particles in diabetic subjects tend to be richer in triglyceride, which makes the particle core more mobile.

The mobility differences are monitored by measuring relaxation rate constants (or time constants) without chemical shifts. Chemical shifts are the centerpiece of conventional high-field, frequency-domain NMR. By contrast, time-domain NMR does not require chemical shifts for frequency domain resolution and does not require high magnetic field strength or field homogeneity. This approach is fundamentally different from conventional NMR spectroscopy in both methodology and instrumentation requirements.

In one embodiment, the invention is a process for measuring the spin-spin or transverse relaxation time constants ($T_2$) for the lipid core compartments in unfractionated human serum. The human serum is obtained in a conventional manner from a low-speed centrifugation of human blood after clotting. Approximately 0.6 mL of unmodified serum is pipetted into a 10 mm NMR tube, and the tube is placed into the bore of the magnet of a bench-top TD-NMR analyzer, typically operating at 10, 20, 40 or 60 MHz resonance frequency for hydrogen. In the examples described here, 20 MHz and 40 MHz data were collected using Bruker benchtop mq20 and mq40 TD-NMR instruments (Bruker BioSpin Corporation, Billerica, Mass., USA).

A Carr-Purcell-Meiboom-Gill (CPMG) pulse sequence is used to measure the exponential time-decay curve. This pulse sequence effectively eliminates chemical shifts and magnetic field inhomogeneity, permitting the measurement of $T_2$ values. Although $T_2$ measurements can be linked with chemical shifts and measured in the frequency domain, the present TD-NMR method measures $T_2$ in the time domain without chemical shifts. This provides a distinct advantage with respect to instrument simplicity and cost.

The resulting $T_2$ decay curve for human serum is multi-exponential, so the individual exponential terms are deconvoluted and resolved with the use of an inverse Laplacian transform. An implementation of this mathematical calculation is provided in the public domain software CONTIN, authored by Steven Provencher (http://s-provencher.com/pages/contin.shtml; accessed Mar. 11, 2013). Under the proper experimental conditions with excellent signal-to-noise, the CONTIN calculation can resolve up to 8 different exponential terms in TD-NMR T2 profiles of human serum. Because human serum has abundant quantities of lipoprotein core lipids and soluble proteins, and because these assemblies are relatively large, the protein and lipoprotein components dominate the $T_2$ profile.

One experimental issue involves solvent suppression, because an intense water signal can overshadow the contributions of lipoprotein components and lead to artifacts such as radiation damping. The solvent water can be partially suppressed using a number of NMR schemes. In this embodiment, a 180-degree pulse and delay is inserted prior to the CPMG sequence. This achieves partial relaxation (and partial suppression) of the water with full recovery of the lipoprotein components by the start of the CPMG pulse scheme. Although there are many sophisticated NMR methods for suppressing water, the goal of this invention was to develop the simplest, most inexpensive method for measuring lipoprotein core properties in unmodified human serum.

Figure 2:
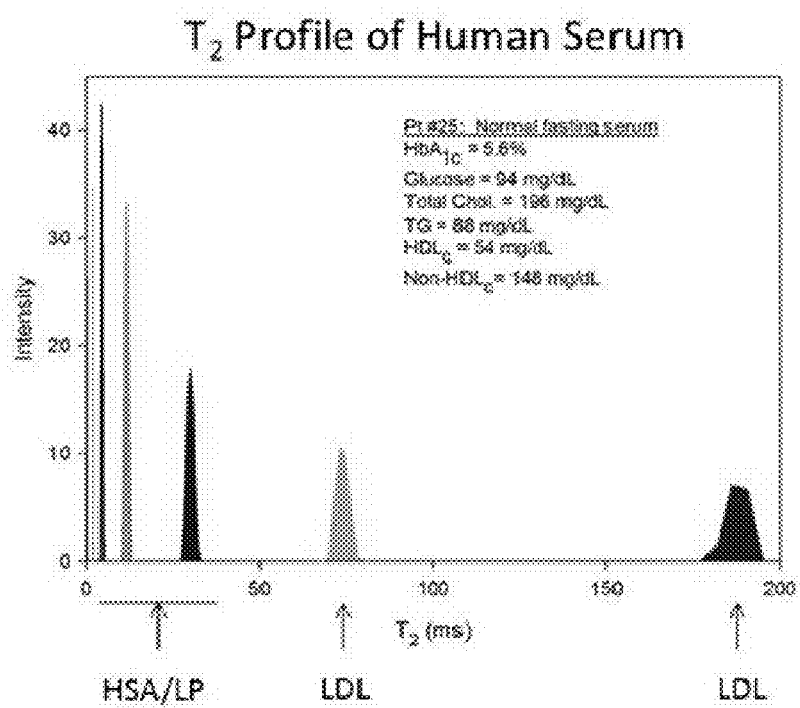
FIG. 2 is a TD-NMR $T_2$ profile for purified human low-density lipoprotein at 25° C.
Figure 3:
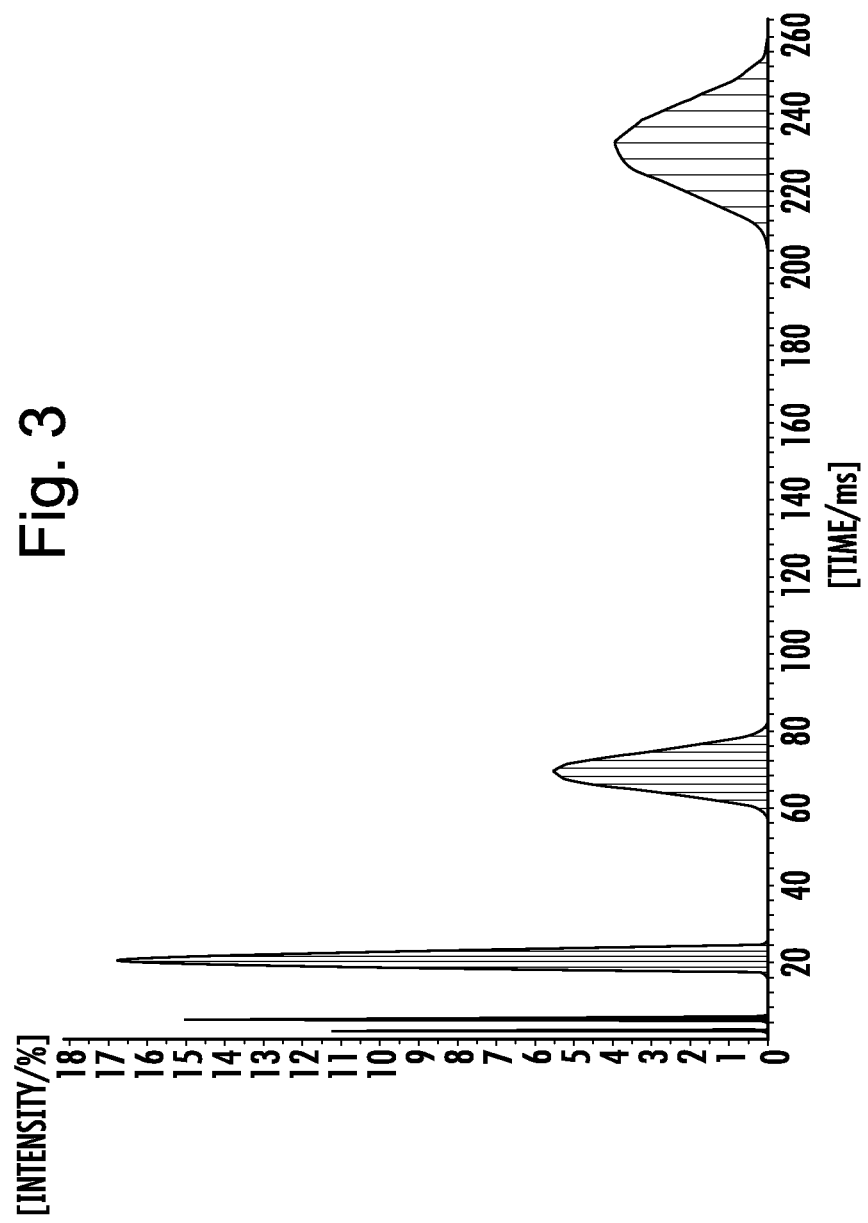
FIG. 3 is a plot of metabolic remodeling of LDL core lipids during metabolism following a meal.

This embodiment is further illustrated using the figures and tables. FIG. 2 shows a time-domain $T_2$ NMR profile of normal fasting human serum, and FIG. 3 is the TD-NMR $T_2$ profile for purified human low-density lipoprotein at 25° C.

The profile of FIG. 2 (not to be confused with a conventional NMR spectrum) was obtained by performing an inverse Laplacian transform of the $T_2$ decay curve. In turn, the $T_2$ curve was measured using a modified CPMG experiment on a Bruker 40 MHz TD-NMR analyzer. The profile resolves 7 distinct $T_2$ components, here represented as peaks in the profile. Higher $T_2$ values represent more mobile elements. The solvent water peak in serum, not shown in this plot, is observed at $T_2$ values of approximately 600 ms. The peaks at approximately 200 and 70 ms represent two distinct mobility domains in LDL, as assigned from control samples containing only LDL.

These two peaks are not observed in the other control samples containing fractionated serum proteins or lipoproteins and appear to provide a unique signature for the core lipid mobility of LDL. The peaks at lower $T_2$ values have contributions from both serum proteins and lipoproteins.

Figure 9:
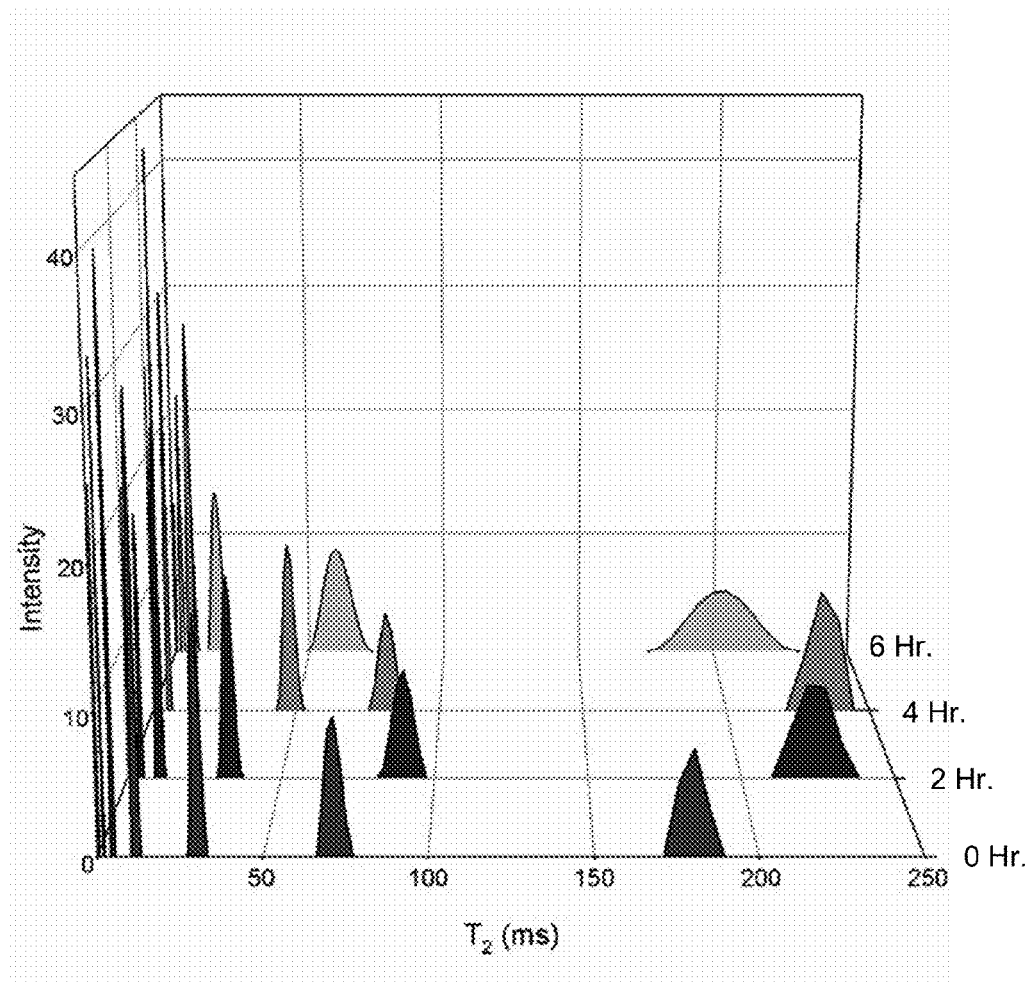
FIG. 9 is a plot of $T_2V$ values for lipoprotein particles at various times after a meal.

FIG. 9 illustrates the variation in $T_2$ measurements in response to metabolic changes following a meal. Shown are $T_2$ profiles for whole human serum at fasting, 2 hours, 4 hours and 6 hours post-prandial. The $T_2$ values for the LDL-specific peaks increase and peak at 4 hours, reflecting the remodeling of the LDL core as the content of triglyceride increases relative to cholesteryl ester.

These preliminary results demonstrate the feasibility of obtaining particle-specific measurements of the core mobility of LDL in whole human serum. The data also demonstrate that $T_2$ measurements obtained from TD-NMR are sensitive to metabolic remodeling and patient-to-patient variability.

Furthermore, the invention requires neither high magnetic field instrumentation nor a frequency-domain analysis. Instead, it uses a time-domain analysis. Unlike (for example) the Otvos approach, the methods of the invention can be performed on inexpensive low-field bench-top instruments, because high field strength and field homogeneity is not required. The key measurables are relaxation rate constants rather than chemical shifts. Differences in relaxation rate constants are used to resolve lipoprotein classes (not chemical shifts, as in Otvos and Kremer). Also, the derived parameter in our invention is lipoprotein particle core mobility or fluidity, rather than particle number or particle size. In summary, the instrumentation, data processing, measurables and derived parameters of our invention are different from those of Otvos.

In contrast to (for example) U.S. Pat. No. 7,550,971, the present invention does not measure analyte concentrations. Rather it measures lipoprotein particle properties, specifically the mobility or fluidity ("squishiness") of the oily lipid core found within lipoprotein particles. Also, the invention is not restricted to low-field, bench-top NMR instruments, but can also be performed on conventional high-resolution NMR instruments as well.

Overall, the method of the invention is much simpler and can be performed on inexpensive low-field benchtop NMR analyzers, and the particle core mobility provides diagnostic information different from particle size and concentration distribution.

ADDITIONAL EXAMPLES

In the following Examples, all aqueous samples are prepared in a 9.1 D2O/H2O saline buffer, concentrated to a viscosity of 1.20 cP at 37° C. The raw data are in the form of a multi exponential decay curve. The individual relaxation time constants are deconvoluted using an inverse Laplacian transform calculation as implemented in the public domain program CONTIN.

Lipoprotein Lipid Core Mixtures

Figure 4:
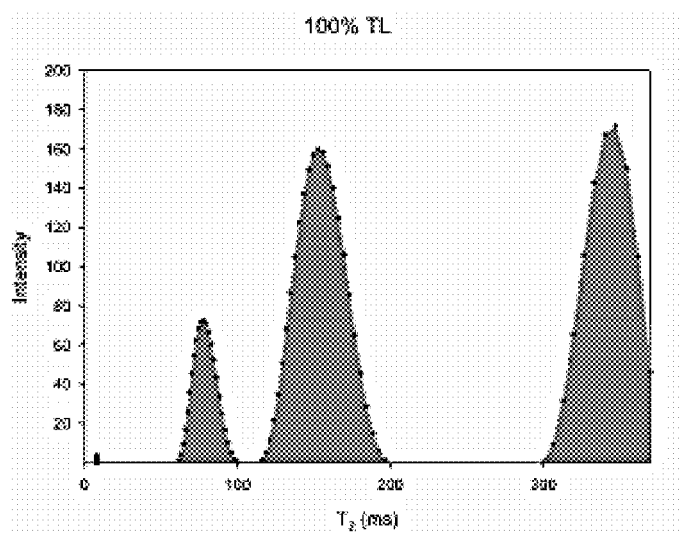
FIGS. 4-6 are CONTIN profiles for pure triolein and for two lipid cores.
Figure 5:
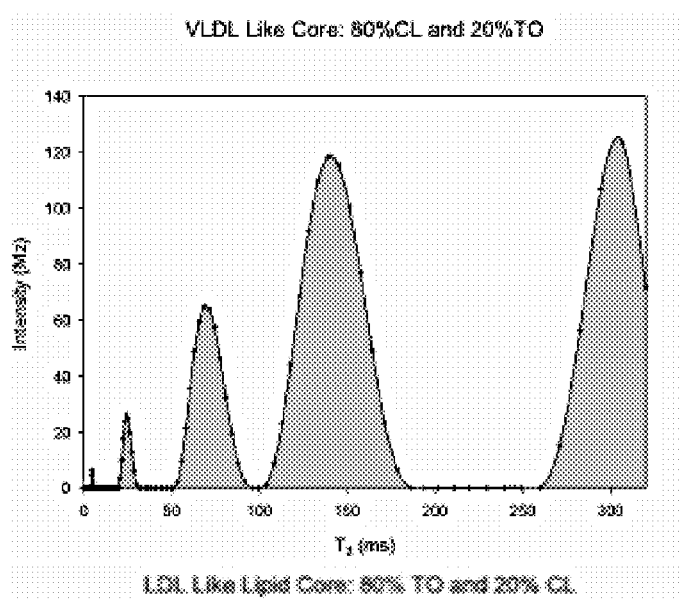
Figure 6:
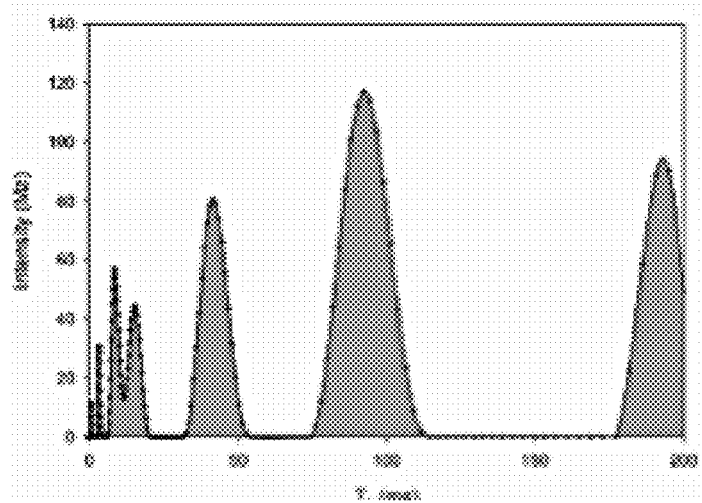

A CONTIN profile of triolein, the most abundant TG in lipoproteins, is shown in FIG. 4. Each $T_2$ (or $T_2V$) corresponds to a mobility domain of the triglyceride molecule. A VLDL like lipid core with 80% TG and 20% CE shows a similar profile (FIG. 5) but is shifted slightly to the left, indicating a less mobile, more vicious environment. The LDL like lipid core (FIG. 6) composed of 80% CE and 20% TG exhibited lower $T_2$ or $T_2V$ values indicating reduced mobility. This trend resembles that observed with physiological lipoprotein particles with differences in TG/CE ratios. $T_2V$ values for lipid mixtures are summarized in Table 1.

TABLE 1

| | (T$_2$V times in ms) | | | |
|---|---|---|---|---|
| | Fast | Medium | Slow | Other |
| 100% TO | 347 | 155 | 79 | 8 |
| 80% to 20% CL (VLDL Core) | 303 | 141 | 70 | 25, 5 |
| 20% to 80% CL (LDL Core) | 183 | 92 | 45 | 19, 9, 4 |

Fractionated Lipoproteins and Serum Proteins

Figure 7:
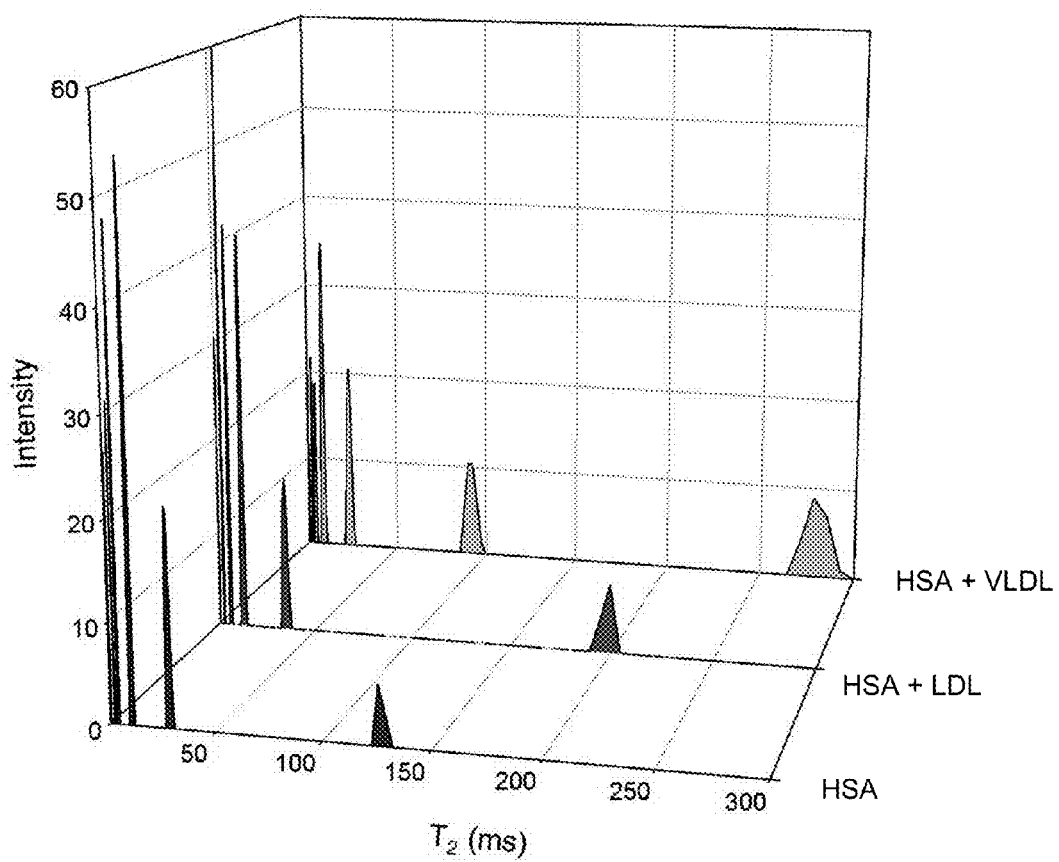
FIG. 7 is a plot of $T_2V$ values for albumin, LDL plus albumin, and VLDL plus albumin.
Figure 8:
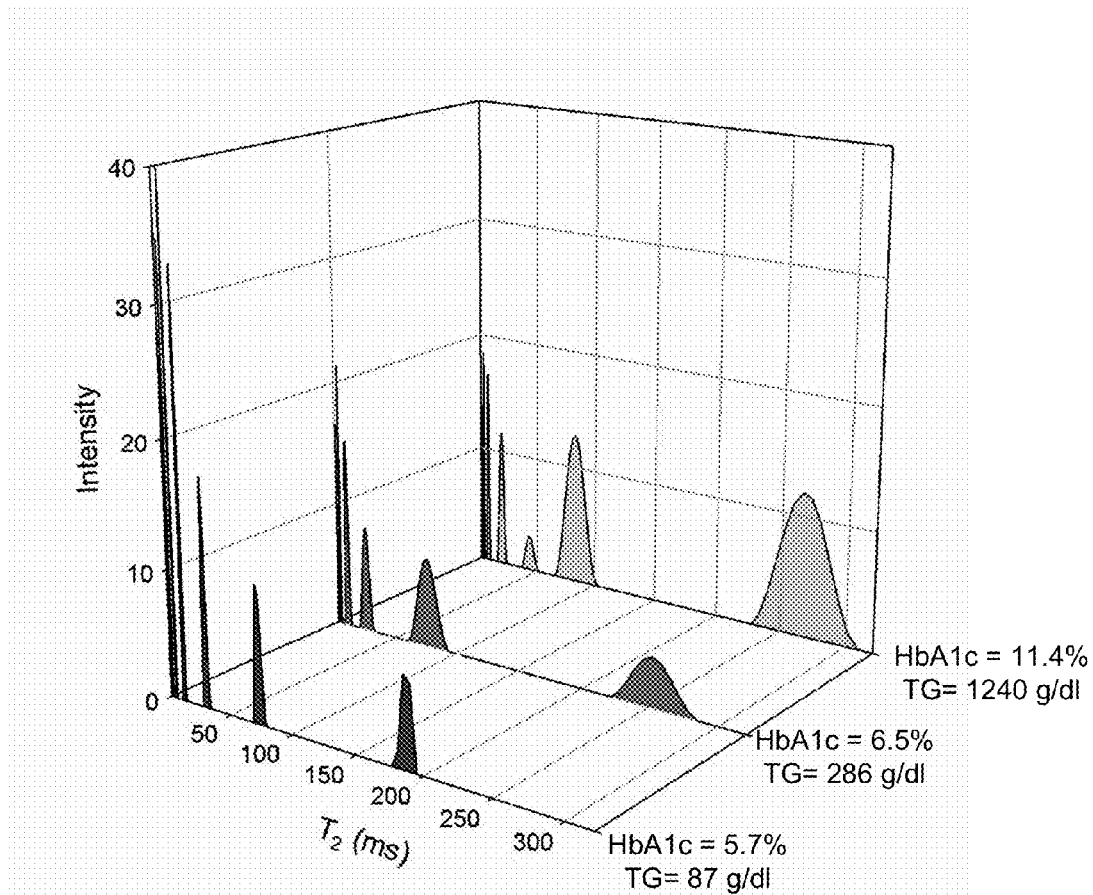
FIG. 8 is a plot of $T_2V$ values for three samples of whole human serum.

FIG. 7 shows the T$_2$V profiles for albumin ("HAS"), LDL plus albumin and VLDL plus albumin. Although all of the profiles display fast decaying components in the range of 2-50 ms, there are T$_2$V values above 50 ms that are unique to individual lipoprotein classes Whole Human Serum De-identified samples of whole human serum, representing various metabolic and disease states were obtained from Pitt County Memorial Hospital (Greenville, N.C., USA). As seen in FIG. 8 variability was observed in lipoprotein T$_2$V values. Patient samples with a higher HbA1c, indicative of poorly managed Type 2 Diabetes Mellitus, have increased T$_2$ or T$_2$V values suggesting that the lipoprotein particles have increasingly mobile, TG-rich lipid cores versus non-diabetic patients.

Results: FIG. 9 shows the remodeling healthy non-diabetic subject ingested a liquid meal that contained 50 grams of lipid following a 16 hour fast, after which blood was drawn every hour for 8 hours. The NMR data are shown in FIG. 4b at 0 hour (fasting) and other time points after the meal. As lipoprotein remodeling occurs and the particles become TG rich, the T$_2$V peak shifts to the right indicating an increase in lipid core mobility. Table 2 shows standard lipid analysis for these samples.

TABLE 2

| | 0 Hr. | 2 Hr. | 3 Hr. | 4 Hr. | 5 Hr. | 6 Hr. | 7 Hr. | 8 Hr. |
|---|---|---|---|---|---|---|---|---|
| Triglycerides | 87 | 184 | 181 | 194 | 197 | 231 | 188 | 169 |
| Cholesterol | 197 | 204 | 200 | 199 | 193 | 187 | 184 | 187 |
| HDL-C | 54 | 55 | 52 | 52 | 49 | 47 | 47 | 48 |
| Non-HDL-C | 148 | 149 | 148 | 147 | 144 | 140 | 137 | 139 |
| LDL-C | 125 | 112 | 112 | 108 | 105 | 94 | 99 | 105 |

Benchtop TD-NMR appears to provide unique information about LDL and VLDL particle properties reflective of different states of normal and abnormal metabolism. This approach holds promise for translation from the research lab into the clinical setting as the measurements are performed on whole human serum and are relatively simple, inexpensive and non-invasive.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method for assessing cardiovascular disease risk based upon the properties of protein and lipoprotein elements in a sample, the method comprising the steps of:
   conducting a low-speed centrifugation of a human blood sample obtained after clotting;
   placing a small volume of the unfractionated human serum sample into a low field TD-NMR spectrometer tuned to measure hydrogen-1;
   applying a series of CPMG spin echo pulse sequences with intermittent delays to the sample in order to measure spin-spin relaxation time constants from the time-domain decay of the signal, without the use of chemical shifts and without converting data into the frequency domain by Fourier transform or other means;
   at least partially suppressing the water signal from the sample by inserting a 180-degree inversion pulse followed by a delay prior to the CMPG sequence used to record relaxation time constants in the time domain;
   analyzing the exponentially decaying NMR signal from the sample in the time domain using multi-exponential analysis; and
   comparing differences in the relaxation time constants for lipoprotein classes selected from the group consisting of LDL, HDL, and VLDL in the sample to measure mobility differences in the oil phases within the core compartment of the selected lipoprotein particles which are in turn reflective of increased cardiovascular disease risk or active disease and in which the comparison of relaxation time constants is made to other relaxation time constants within a group consisting of samples from the same human subject and samples among different human subjects.

2. A method according to claim 1 comprising using between about 0.2 and −0.6 mL of the sample.

3. A method according to claim 1 further comprising normalizing the viscosity of the sample.

* * * * *